United States Patent [19]

Halvorsen

[11] E Patent Number: Re. 32,204

[45] Reissued Date of Patent: Jul. 15, 1986

[54] ELECTRODE ASSEMBLY FOR TEMPORARY PACING AND HEART MEASUREMENTS

[75] Inventor: Kenneth Halvorsen, San Clemente, Calif.

[73] Assignee: Mansfield Scientific, Inc., Mansfield, Mass.

[21] Appl. No.: 499,803

[22] Filed: Jun. 1, 1983

Related U.S. Patent Documents

Reissue of:

[64] Patent No.: 4,289,138
Issued: Sep. 15, 1981
Appl. No.: 157,504
Filed: Jun. 9, 1980

[51] Int. Cl.[4] ..... A61B 5/04

[52] U.S. Cl. ..... 128/642; 128/419 P; 128/786

[58] Field of Search ..... 128/419 P, 639, 642, 128/692, 784, 786

[56] References Cited

U.S. PATENT DOCUMENTS

| | | | |
|---|---|---|---|
| 623,022 | 4/1899 | Jonnson | 128/786 |
| 3,347,224 | 10/1967 | Adams | 128/692 |
| 3,788,329 | 1/1974 | Friedman | 128/419 P |
| 3,825,015 | 7/1974 | Berkovits | 128/419 P |
| 3,865,118 | 2/1975 | Bures | 128/419 P |
| 3,866,615 | 2/1975 | Hewson | 128/784 |
| 3,949,757 | 4/1976 | Sabel | 128/419 P |
| 4,011,875 | 3/1977 | Lehr | 128/419 P |
| 4,057,067 | 11/1977 | Lajos | 128/419 P |
| 4,112,952 | 9/1978 | Thomas et al. | 128/419 P |
| 4,135,518 | 1/1979 | Dutcher | 128/419 P |
| 4,164,939 | 8/1979 | Kolin | 128/692 |

FOREIGN PATENT DOCUMENTS

| | | |
|---|---|---|
| 2605590 | 8/1977 | Fed. Rep. of Germany . |
| 2918741 | 4/1980 | Fed. Rep. of Germany . |
| 2180908 | 11/1973 | France . |
| 2421626 | 11/1979 | France . |
| 0009732 | 9/1979 | PCT Int'l Appl. . |
| 0806013 | 12/1958 | United Kingdom . |
| 1119615 | 7/1968 | United Kingdom . |
| 1123137 | 8/1968 | United Kingdom . |
| 1401477 | 7/1975 | United Kingdom . |
| 1416197 | 12/1975 | United Kingdom . |
| 1424355 | 2/1976 | United Kingdom . |
| 1432233 | 4/1976 | United Kingdom . |
| 1490585 | 11/1977 | United Kingdom . |
| 1499520 | 2/1978 | United Kingdom . |

*Primary Examiner*—William E. Kamm

[57] ABSTRACT

An electrode assembly for use with a catheter, is made of a plurality of insulated wires. The wires are bound together in a bundle by fine insulated wire for almost their entire lengths. At one end of the bundle are free wire ends of different lengths on which are electrically conductive ferrules. The ferrules are spaced apart axially when aligned with the bundle inside the catheter. The wires are made of springy material so that the free wire ends separate widely outside the catheter. Other cylindrical ferrules are mounted in axially spaced position on bared portions of the other end of the bundle, and encircle all the wires, but each ferrule is in direct electrical contact with only one of the wires.

13 Claims, 10 Drawing Figures

8
24
12
26
8
40
12a
12b
40
10
42
14
41
LA
RA
45
46
16b
LV
RV
46
18
16a
44

10

16a
24
40
12
16b
23
40
18
12'
12a
48
4
4
12b 20
12'

12a
12
48'
A
14
12b

A
14
12a
12
16a
12b 16b
20
23
18
24
12a
22
16a 34
30
24
32
20
12a
14
38
26
39
12b
12
36

ELECTRODE ASSEMBLY FOR TEMPORARY PACING AND HEART MEASUREMENTS

Matter enclosed in heavy brackets [ ] appears in the original patent but forms no part of this reissue specification; matter printed in italics indicates the additions made by reissue.

This invention concerns an electrode assembly adapted for temporary heart pacing and making measurements of blood vessels.

A generally known typical catheter type flow sensor adapted for temporary pacing applications is comprised of a bifilar probe terminating in a wire loop in a lenticular shape. The loop is collapsed when inside the catheter and when it leaves the catheter and enters into a chamber of the heart or into a blood vessel it takes a lenticular shape. When the loop is withdrawn into the catheter, there is always the hazard that a leaf of a heart valve or other protrusion will be caught in the loop.

The present invention is directed at overcoming the above and other difficulties and disadvantages of the prior loop type of catheter probes, and for providing an improved electrode assembly which can employ a catheter of smaller external diameter than that required by loop types of probes.

According to the invention there is provided an electrode assembly which can function as a temporary heart pacer as well as an instrument for measuring the flow in blood vessels. The assembly may employ insulated bifilar, trifilar, quadrafilar or the like wire terminating in free ends of different lengths. On the end of each wire is a ferrule. The ferrules are staggered or spaced in position lengthwise of and inside a catheter during insertion through the catheter, which may be positioned into a heart chamber via a blood vessel. The internal diameter of the catheter required to accomodate the ferrules and adjacent wires of the bifilar, trifilar or quadrafilar wire is less than required to accomodate a wire loop of a corresponding loop type probe.

It is therefore, a principal object of the present invention to provide an electrode assembly for use in making heart measurements and or temporary pacing, wherein the wires terminate in free ends, rather than in the prior known closed wire loop.

Another object of the present invention is to provide an electrode assembly of the type described wherein the free ends of the wires have different lengths.

A further object of the present invention is to provide an electrode assembly as described, wherein ferrules are secured to the free ends of the wires, and wherein further ferrules are mounted on the other ends of the wires.

These and other objects and many of the attendant advantages of this invention will be readily appreciated as the same becomes better understood by reference to the following detailed description when considered in connection with the accompanying drawings in which.

Figures 1, 2, 3, 4, 5, 6, 7, 8:
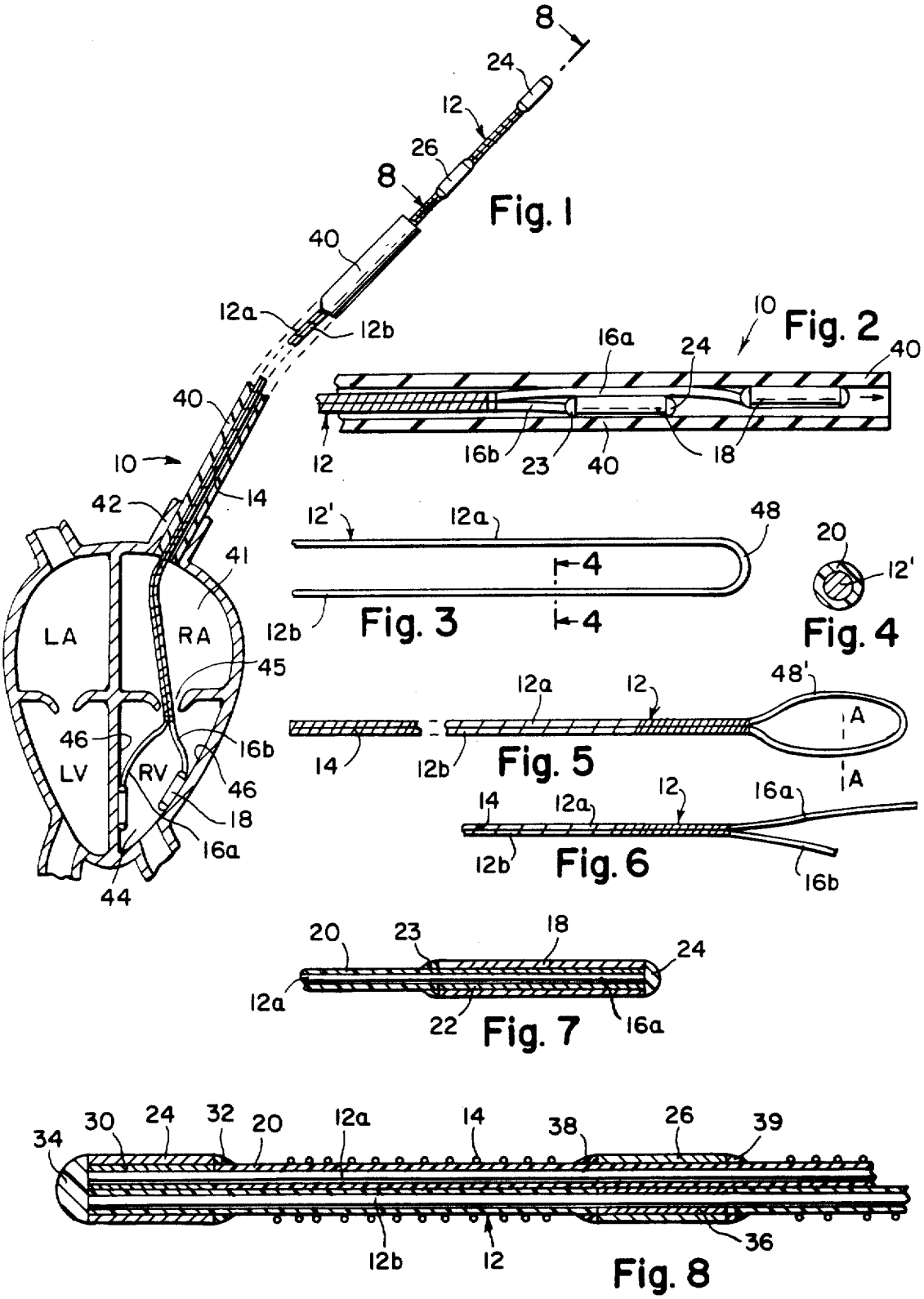
FIG. 1 is a side elevational view of an electrode assembly embodying the invention, parts being shown in section and other parts being broken away to show internal construction.
FIG. 2 is an enlarged longitudinal sectional view of an end portion of the electrode assembly.

FIGS. 3, 5, and 6 are plan views showing the wires at successive stages of assembly;

FIG. 4 is an enlarged cross section taken along line 4—4 of FIG. 3;

FIG. 7 is an enlarged axial sectional view of one end of the electrode assembly;

FIG. 8 is an enlarged axial view of the other end of the electrode assembly taken along line 8—8 of FIG. 1.

Figure 9:
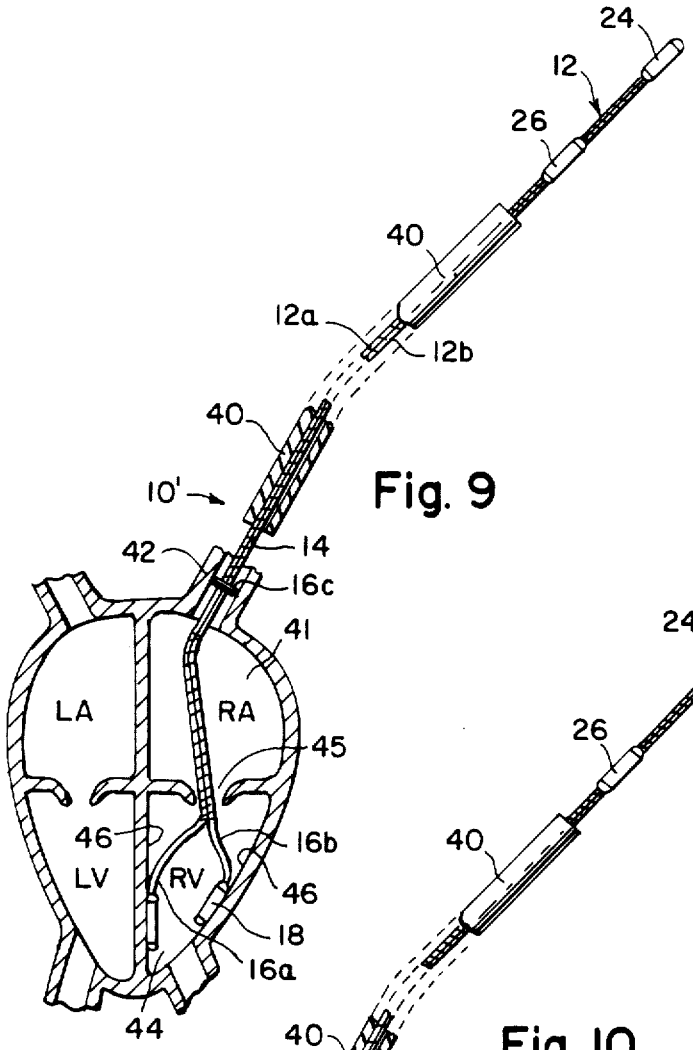
Figure 10:
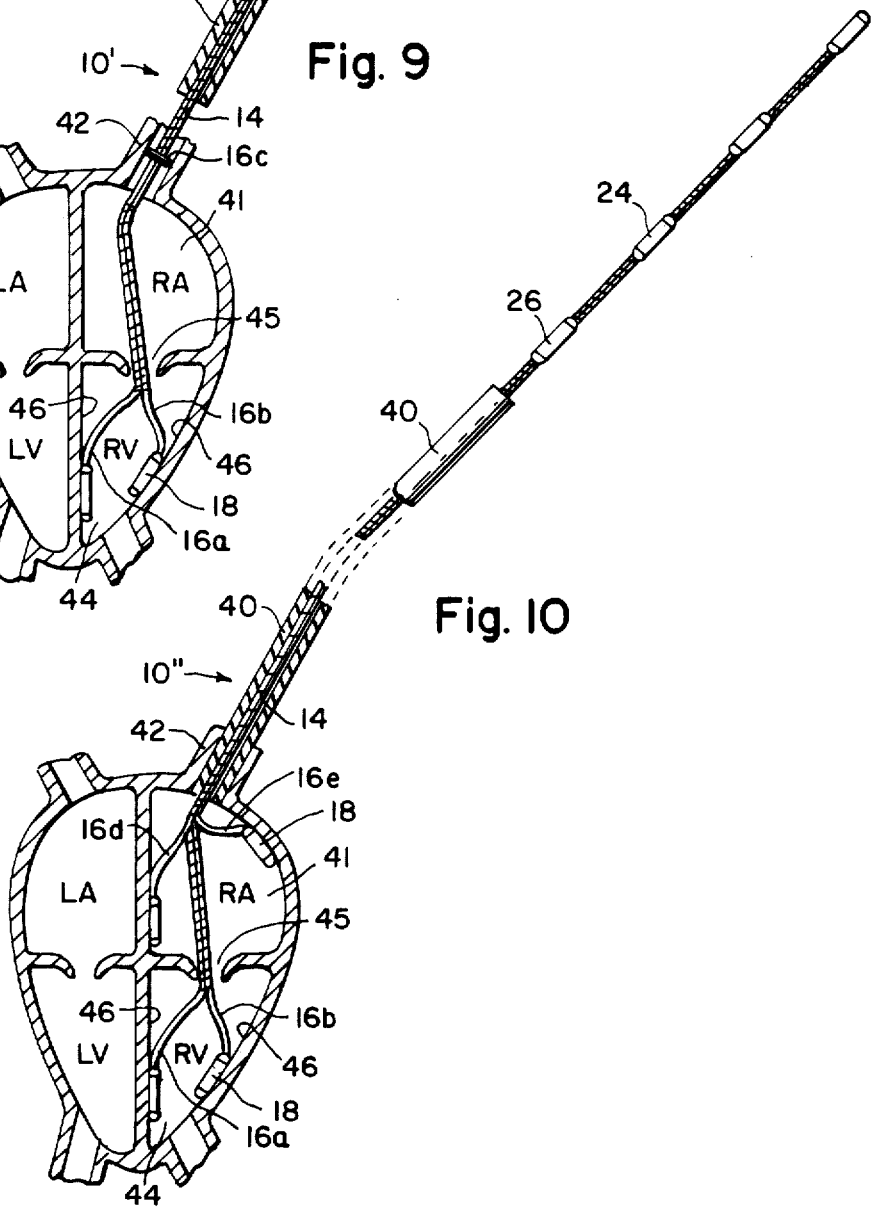

FIG. 9 is another embodiment of the electrode assembly 10' similar to FIG. 1; and FIG. 10 is a further embodiment of the electrode assembly 10''.

Referring now to the drawings wherein like reference characters designate like or corresponding parts throughout, there is illustrated in FIG. 1, an electrode assembly, generally designated as reference numeral 10 which includes a pair of insulated wires 12a, 12b bound together in a bifilar array 12 by an insulated fine wire winding 14. The winding 14 terminates short of the free ends 16a, 16b of the bifilar array 12. The end 16a is longer than the end 16b. A ferrule 18 is mounted on each of the wire ends 16a, 16b. As best shown in FIG. 7, the ferrule 18 has a cylindrical metal body into which the end 16a or 16b of the respective wire 12a or 12b is inserted. A coat of insulation 20 on the wire 12 is scraped away at the wire end and a conductive cement 22 such as silver filled epoxy is applied to the bare wire end on which is axially mounted cylindrical ferrule 18. At both ends of the ferrule 18 are applied a respective bead 23, 24 of an insulation material such as epoxy.

At the other end of the bifilar array 12 are two further cylindrical ferrules 24 and 26; see FIGS. 1 and 8. These ferrules may be connected to an external electrical circuit. Ferrule 24 is mounted on the other end of bifilar wires 12a, 12b. The insulation 20 is scraped away from the end of the wire 12a, and the bared wire is coated with a conductive cement 30 to secure the ferrule 24 on the wire end. The ferrule 24 encircles both wires 12a, 12b, but is insulated from the wire 12b. Beads 32, 34 of an insulation cement are placed at opposite ends of the ferrule 24. Axially spaced from the ferrule 24 is the cylindrical ferrule 26. Insulation 20 is scraped away from a portion of wire 12b and the ferrule 26 is mounted on the bifilar wires 12a and 12b and secured in place on the bared portion of wire 12b by a conductive cement 36. A respective bead 38, 39 of insulation cement is applied to an opposite end of the ferrule 26. The binding wire 14 is also removed from the portions of the bifilar wires 12a and 12b carrying the ferrules 24 and 26.

FIG. 2 shows the ferrules 18 disposed in longitudinal spaced position inside a flexible catheter 40. In operation, the flexible catheter 40 may be inserted through a vein 42 (FIG. 1) through the right atrium 41 to the tricuspid valve 45. The electrode assembly 10 will pass axially through the catheter 40 and out of its free end through the tricuspid valve 45 into the right ventricle 44. There the free end of the bifilar wire probe will separate and the ferrules 18 will contact the opposite spaced walls 46 of the right ventricle 44. The catheter 40 may then be removed from the heart.

FIGS. 3 and 4 show one step in the method of fabricating the electrode assembly. Fine springy wire 12' made of beryllium copper or beryllium nickel or other suitable alloy ranging from 0.004" to 0.125" is coated with an insulating layer 20 such as polyurethane varnish. The wire 12' is bent to form a loop 48. Then the wire sections 12a and 12b are placed side-by-side as shown in FIG. 5 and wound with the fine binding wire 14 such as 0.002" insulated copper wire. The binding wire 14 may be bonded to the wire sections 12a and 12b with several cured coats of an insulated material (not shown), such as polyurethane varnish which was used for the insulation 20. The loop 48' is then cut on line A—A so that the wire end 16a will be longer than the wire end 16b as shown in FIG. 6. Then the insulation 20 is scraped from the wire ends 16a and 16b and the ferrules 18 are mounted on the wire ends 16a, 16b as shown in FIGS. 1 and 7. The lengths of the wire ends 16a and 16b are critical. One wire end 16a should be longer than the other end 16b by at least the length of one ferrule 18, so that the ferrules occupy minimum space inside the catheter 40. The axial spacing of the contact ferrules 18 permit the ferrules 18 to pass through a smaller catheter 40 than would be needed if both of the ferrules 18 were in a side-by-side position against each other when passing through the catheter 40.

The arrangement described provides better contact between the walls of the chamber 44 than prior loop type probes. The free ends of the wires can open wider than maximum diameter of a prior closed loop type of probe. The ferrules 18 make a better contact with the chamber walls than the narrow sides of a closed wire loop because the ferrules have a larger surface area than the electrodes of the prior loop type catheter probe. Furthermore, the free wire ends will not catch on protrusions in the chamber walls as presently possible with closed wire loops. In addition, the free wire ends bearing ferrules 18 will pass through a catheter of narrower diameter than one sized to accomodate a probe with closed wire loop. The use of a catheter of narrower diameter facilitates passage of the catheter through vessels of the body such as chambers of the heart, or to other organs.

FIG. 9 illustrates another embodiment of the electrode assembly 10' wherein the binding wire 14 has been formed into a terminal 16c in order to have bipolar pacing. That is to say, when the electrode assembly 10 of FIG. 1 is pulsed by a D.C. Voltage each of the terminals 16a and 16b have a different polarity. On the other hand, in the electrode assembly 10'' of FIG. 9, the terminal 16a and 16b may have one polarity and the terminal 16c which is located in the blood vessel just outside of the heart has the other polarity or terminal 16a and 16c may have the same polarity and terminal 16b the other polarity or terminal 16b and 16c may have the same polarity and terminal 16a the other polarity. It should be noted that for bipolar pacing, the terminal 16c must be located outside of the heart.

In some instances, it may be desirable to have a sequential atrial and ventricular pacing. For this purpose, an electrode assembly 10'' as illustrated in FIG. 10 may be utilized. The electrode assembly 10'' may be made from quadrafilar wires and is comprised of terminals 16a, 16b, 16d, and 16e. The terminals 16d and 16e are identical to the terminals 16a and 16b respectively. The other end of the electrode assembly 10'' has four ferrules each substantially the same as the ferrules 24 or 26. In operation for sequential atrial and ventricular pacing, the catheter 40 is inserted through the right atrium to the tricuspid valve as before. The electrode assembly 10' is passed through the catheter 40 so that the electrode 16a and 16b extend into and contact the walls of the right ventricle. The catheter 40 is then removed and as it leaves the right atrium, the terminals 16d and 16e which as mentioned before are identical respectively to the terminals 16a and 16b, expand and contact the atrium walls. The pulsed D.C. voltage may be applied to the ferrules at the end of the electrode assembly 10'' to pulse the right atrium terminals 16d and 16e and then the right ventricular terminals 16a and 16b in sequence to imitate the normal heart function.

Although not illustrated, the electrode assembly may be used to determine the contractility of the left ventricle after a myrocardial infarction, by an electrode assembly (using 0.004" diameter wires) placed in a catheter which has been introduced through a mitral valve in the left ventricle. A radio-opaque dye may then be pumped through the catheter into the left ventricle and the electrode assembly may be pulsed when the heart is depolarized so that the contraction is greater than that which exists during a normal heart cycle. The contraction of the heart may be filmed and will display a measure of the damage of the heart by the infraction. It may also be understood that the aforementioned electrode assembly may be used as an EKG Monitor in the ventricle and can then be switched when fibrillation occurs as a defribrillator.

In view of the foregoing, it is clear that by having wires of different lengths, a trifilar, quadrafilar or any bundle of wires will pass through a substantially smaller diameter catheter than that required for the prior art loop type catheter probe. It would also be noted, that the electrode assembly hereinbefore described, may be used for measurement of blood flow in a vessel in which the assembly is placed, in much the same manner as that of a loop type catheter probe.

It should be understood that the foregoing relates to only a preferred embodiment of the invention, and that it is intended to cover all changes and modifications of the example of the invention herein chosen for the purposes of the disclosure, which do not constitute departures from the spirit and scope of the invention.

What is claimed is:

1. An electrode assembly for insertion into a catheter and establishing an electrical connection to an electronic circuit, said assembly comprising:

a plurality of wires, each of said wires insulated from each other and each of said wires being electrically conductive and extending together side-by-side and having different lengths at one end thereof; [an insulated other wire] *means* binding said plurality of wires together for substantially their entire length except for a free end at said one end of each of said wires;

an end portion of each of said free ends being bared of insulation;

an electrically conductive ferrule positioned on each of said bared portions on each of said free ends of said wires, said ferrules being spaced apart axially of each other when axially aligned with said free ends of said wires inside said catheter; and a conductive means for connecting the other ends of each of said wires to said electronic circuit.

2. An electrode assembly as defined in claim 1, wherein said wires are made of springy material so that said free ends separate widely outside of said catheter.

3. An electrode assembly as defined in claim 1, further comprising insulation material forming insulative beads at opposite ends of each cylindrical ferrule.

4. An electrode assembly as defined in claim 3, wherein said conductive means comprises electrically conductive other elements positioned on bared portions of other ends of each of said wires.

5. An electrode assembly as defined in claim 4, wherein said [outer] *other* conductive elements are spaced apart axially of each other on each of said wires.

6. An electrode assembly as defined in claim 5, wherein each of said other conductive elements in another cylindrical ferrule each enclosing each of said wires but electrically contacting only one of said wires.

7. An electrode assembly as defined in claim 6, wherein each of said other ferrules is held in place by conductive material on said wires.

8. An electrode assembly as defined in claim 1 wherein said plurality of wires is bifilar.

[9. An electrode assembly as defined in claim 1, wherein said other wire is formed as another contact element and is axially spaced between said ferrules and other ends of said wires.]

10. An electrode assembly as defined in claim 1, wherein said plurality of said wires is quadrafiler.

*11. An electrode assembly as defined in claim 1 wherein said means binding said plurality of wires together is an insulated other wire.*

*12. An electrode assembly is defined in claim 11, wherein said other wire is formed as another contact element and is axially spaced between said ferrules and other ends of said wires.*

*13. In an electrode assembly for insertion into the heart of a person via a catheter or the like for establishing an electrical connection between heart tissue and an electronic circuit, said assembly comprising at least two wire leads insulated from each other and carrying relatively large contact portions on their ends, said wire leads being slidable relative to said catheter, the improvement wherein*

*said wire leads are bound together in a manner providing discrete free distal end portions of fixed relative length,*

*said free end portions of said wire leads comprising oppositely bent springs that carry said relatively large contact portions,*

*when residing within said cannular passage, said wire portions being temporarily straightened in a manner known per se by the confining walls of said cannular passage, and lying alongside one another,*

*the fixed lengths of the free end portions of said wires being of preselected, only slightly different length in a manner to stagger within the cannular passage the positions of the relatively large contact portions, thereby to enable said cannular passage to be of minimum diameter,*

*whereby said assembly can enter via a single cannular passage to position multiple wire leads within one cavity of the heart, and*

*said free end portion of said wires can spring apart to their original bent shape within said one heart chamber upon relative withdrawal of said cannular passage, thereby to enable stable contact of said contact portions at multiple positions within a relatively small region of the heart.*

*14. The electrode assembly of claim 13 wherein at the other end of the assembly a number of axially spaced apart contact portions encircle all the wire ends, each of said contact portions being in direct electrical contact with only one of said wire leads.*

* * * * *